United States Patent [19]

Suzuki et al.

[11] Patent Number: 4,473,842

[45] Date of Patent: Sep. 25, 1984

[54] APPARATUS AND METHOD FOR EXAMINING PRINTED CIRCUIT BOARD PROVIDED WITH ELECTRONIC PARTS

[75] Inventors: Etsuji Suzuki, Tokyo; Shinichi Uno, Kawasaki; Kiyomu Chiyoda, Ayase; Mitsugi Nakanoya, Yokohama, all of Japan

[73] Assignee: Tokyo Shibaura Denki Kabushiki Kaisha, Kawasaki, Japan

[21] Appl. No.: 393,653

[22] Filed: Jun. 30, 1982

[30] Foreign Application Priority Data

Jul. 6, 1981 [JP] Japan .................................. 56-105331
Apr. 20, 1982 [JP] Japan .................................. 57-64691

[51] Int. Cl.³ ............................................. H04N 7/18
[52] U.S. Cl. .................................... 358/107; 358/106; 358/101
[58] Field of Search ........................ 358/101, 106, 107

[56] References Cited

U.S. PATENT DOCUMENTS 4,253,111 2/1981 Funk .................................... 358/101
4,295,198 10/1981 Copeland ............................ 358/101

FOREIGN PATENT DOCUMENTS 1582388 1/1981 United Kingdom .

Primary Examiner—Howard W. Britton
Attorney, Agent, or Firm—Oblon, Fisher, Spivak, McClelland & Maier

[57] ABSTRACT

Image data of lead terminals and a chip element provided on a circuit board are stored on a video memory. Part of the video data stored in the video memory is read out and stored in a RAM by a microprocessor to be compared with reference pattern data stored in an external memory. The position of the chip element is checked in this way by having reference to the lead terminals.

9 Claims, 5 Drawing Figures

APPARATUS AND METHOD FOR EXAMINING PRINTED CIRCUIT BOARD PROVIDED WITH ELECTRONIC PARTS

BACKGROUND OF THE INVENTION

This invention relates to apparatus and method for examining a printed circuit board provided with electronic circuit elements and, more particularly, to those for checking whether a miniaturized electronic element mounted on a circuit board is at a correct position.

Recently, electronic parts in the form of chip elements, such as miniaturized electronic elements, have become popular and are replacing electronic parts with leads. Such chip elements are often mounted on circuit boards together with electronic parts with leads. When assembling such a circuit, chip elements are first temporarily bonded by adhesive to a circuit board at given locations thereof and, after the adhesive is cured in a drying chamber, the chip elements are permanently soldered. Where electronic circuits are produced on a mass production basis, the temporary bonding of chip elements on the circuit board is carried out on an automatic assembly line.

In this case, it is likely that chip elements are mounted in deviated positions or detached from a given position on the circuit board. If such a defectiveness is found after the soldering, the position-correction is very time-consuming, thus increasing the cost of manufacture of the apparatus using the circuit board or reducing the yield. Therefore, it is very important to find out a chip element temporarily bonded in an incorrect position or a missing chip element and take necessary correction measures before regularly soldering the chip elements.

Usually, the checking for chip elements out of right positions and missing chip elements is carried out by visual checking, which requires a great deal of man-hour and is inefficient and poorly reliable.

It has been proposed to check for chip elements out of right positions and missing chip elements by processing image data of the circuit board carrying bonded chip elements that is obtained with an image pick-up camera. In this case, however, if the circuit board that is to be checked is set in an incorrect position or if there is a warp or like deformation of the circuit board itself, accurate position inspection cannot be obtained.

SUMMARY OF THE INVENTION

An object of the invention is to provide apparatus and method for examining printed circuit board provided with miniaturized electronic parts, which can determine the position of miniaturized electronic parts temporarily attached to a circuit board accurately without being influenced by the deviation of the circuit board from the setting position or by the warp or like deformation of the circuit board.

According to the invention, this object is achieved by a position examination apparatus, which comprises means for directing light onto one side of a transparent circuit board to provide light passed therethrough, means receiving light from the circuit board to obtain a signal representing the line scanned image of the circuit board, an analog-to-digital converter for converting the image signal thus obtained into digital image data, a video memory for storing said digital image data, external means for providing reference pattern data of a unit area including a miniaturized electronic parts in a predetermined position on said circuit board, and control means for checking for the positional deviation of a chip element with respect to a reference mark provided on the circuit board by reading out digital image data corresponding in position to said reference pattern data from a video memory and comparing the read-out data with the reference pattern data.

DETAILED DESCRIPTION OF THE PREFERRED EMBODIMENT

Figure 1:
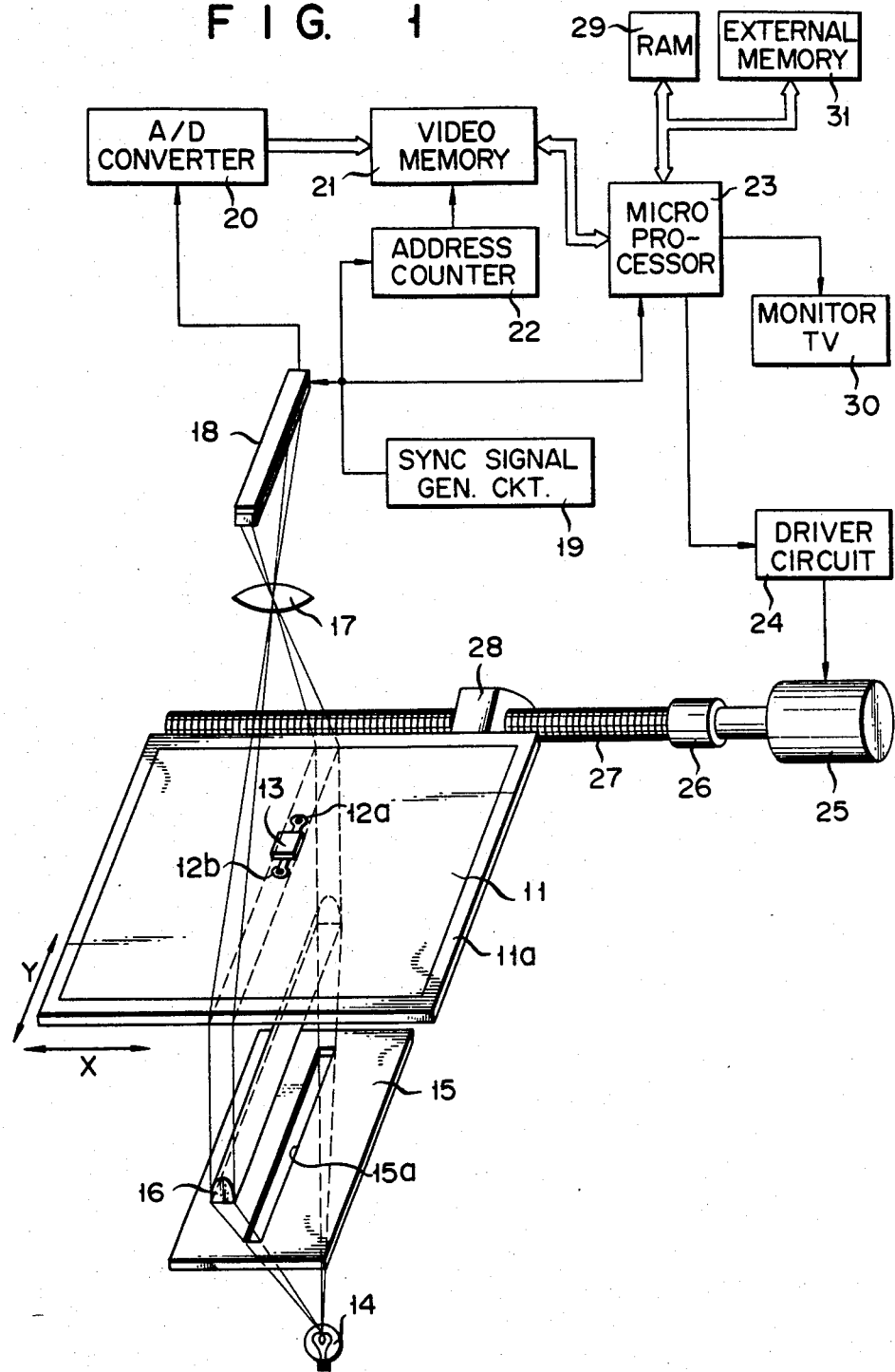
FIG. 1 is a schematic representation of one embodiment of the invention.

Now, an embodiment of the invention will be described in detail with reference to the drawings. FIG. 1 is a block diagram showing one embodiment of the invention applied to an apparatus for checking whether a chip element 13 such as a semiconductor device and a resistor element is temporarily bonded by an adhesive to a semi-transparent insulating circuit board 11, for instance made of an epoxy resin, in a correct position between printed lead terminals 12a and 12b which are formed on the circuit board 11 held on a support frame 11a. The circuit board 11 is illuminated from the lower side thereof by a lamp 14 over its entire dimension in the direction shown by arrow Y. More particularly, light from the lamp 14 is illuminated through a narrow slit 15a of a slit plate 15 to be incident on a cylindrical lens 16. Light incident on the cylindrical lens 16 is converted to a parallel light beam, which is projected onto the lower side of the circuit board 11.

The lead terminals 12a and 12b are made of copper foils so that they are absolutely non-transparent, and the chip element 13 is also non-transparent. On the other hand, the circuit board 11 is semi-transparent. A light image that conforms to the lead terminals 12a and 12b and chip element 13 is thus focused on an image sensor 18 through a lens 17. The image sensor 18 may be a photodiode array, a CCD image pick-up device or the like, and a light image of a portion of the circuit board 11 covering the entire dimension thereof in the direction of arrow Y is incident as image of one line and converted to a corresponding electric signal. In the image sensor 18, line scanning at a predetermined scan rate is performed according to a clock signal supplied from a synchronization signal generating circuit 19.

The electric signal representing the image of one line, obtained from the image sensor 18, is converted by an analog-to-digital converter 20 into a digital video data which is supplied to a video memory 21. The video memory 21 has M×N memory locations and can store video data of whole area of the circuit board 11. The addresses of these memory locations are specified by an address counter 22, which counts the clock signal supplied to the image sensor 18. Thus, the video data of a particular area in which the chip element 13 is bonded, obtained through the line scan in the image sensor 18 is stored as 64 unit data or successive image data in the Y-direction of the circuit board 11 in the respective memory locations.

The clock signal from the synchronization signal generating circuit 19 is also supplied to a microprocessor 23. Each time the video data for one line has been stored in the video memory 21, the microprocessor 23 provides a drive pulse to a drive circuit 24. The driver circuit 24 drives a pulse motor 25 according to the input drive pulse. The shaft of the pulse motor 25 is coupled to a feed screw 27 through a coupling 26. Screwed on the feed screw 27 is a nut 28, to which the support frame 11a of the circuit board 11 is secured. The circuit board 11 is thus driven at a predetermined rate in the direction of arrow X with a rotation of the pulse motor 25. Thus, when the circuit board 11 has been moved over the cylindrical lens 16 in the direction of the arrow X from its position, at which its one end in this direction is in register with the cylindrical lens 16, to its position, at which its other end is in register with the lens 16, video data for the entire surface of the circuit board 11 is completely stored in the video memory 21.

Figure 2:
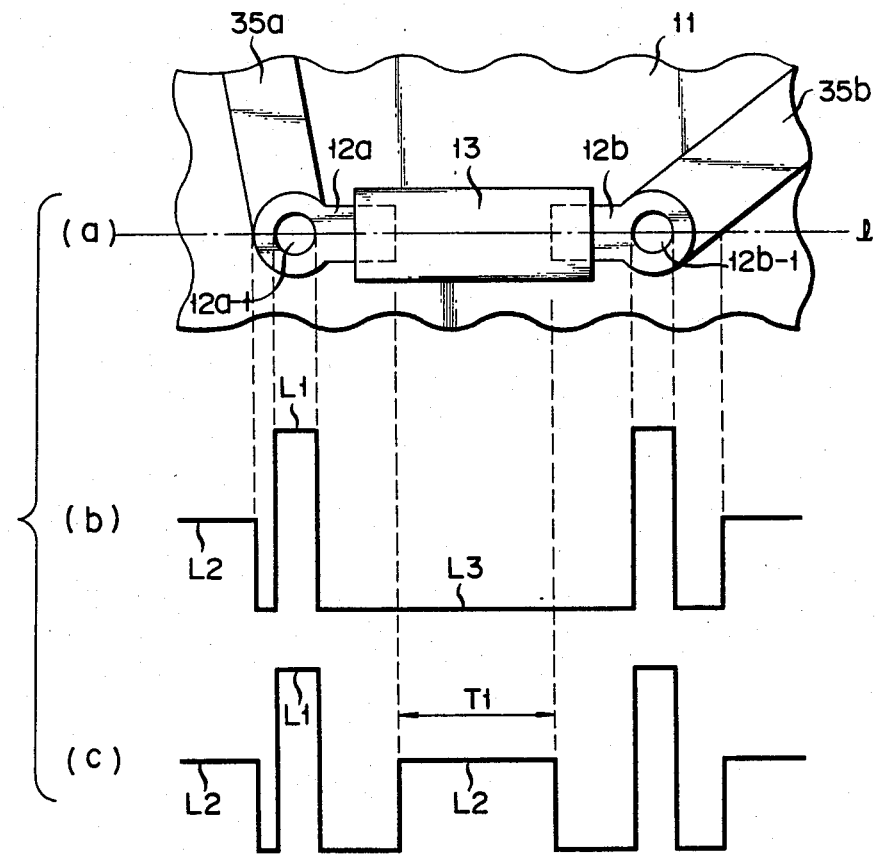
FIG. 2 is a view showing the intensity of incident light on an image sensor concerning a pair of lead terminals and a chip element in FIG. 1.

The video data stored in the video memory 21 is supplied to a RAM 29 and a monitor television set 30 under the control of the microprocessor 23. To the microprocessor 23 is also coupled an external memory, for instance a floppy disk memory 31. In the floppy disk memory 31, data concerning the right positions of the lead terminals 12a and 12b and also the chip element 13 on the circuit board 11 are preliminarily stored as a reference pattern data. While only a single pair of lead terminals 12a and 12b and a single chip element 13 are shown in FIG. 1 for the sake of simplicity; actually a plurality of lead terminal pairs are formed on the circuit board 11. In this embodiment, round see-through holes 12a-1, 12b-1 (see FIG. 2) are formed on the individual lead terminals 12a, 12b and circuit board 11, and the positions of the lead terminals 12a, 12b are detected by making use of the fact that light passed through the round holes 12a-1, 12b-1 reaches the image sensor 18 as the most intense light.

FIG. 2(a) shows the lead terminals 12a and 12b which have the round see-through holes 12a-1 and 12b-1 which are formed in their portions having an increased dimension. The circuit board 11 is also formed with see-through holes which correspond to the see-through holes 12a-1 and 12b-1. An elongate chip element 13 is bonded to the circuit board 11 between the opposed ends of the lead terminals 12a and 12b. Thus, with the circuit board 11 illuminated by light from its lower side as shown in FIG. 1, the intensity of light incident on the image sensor 18 is highest as shown at L1 in portions thereof corresponding to the see-through holes 12a-1 and 12b-1. for light directly reaches the sensor 18 through these holes. On the other hand, substantially no light passes through the lead terminals 12a and 12b and chip element 13, so that the intensity of light incident on the corresponding portions of the sensor 18 is lowest, as shown at L3. If there are printed conductors 35a and 35b which are leading from the lead terminals 12a and 12b, the intensity of light incident on the corresponding portions is also L3. The circuit board 11, which is made of a transparent epoxy resin, transmits a certain amount of light, and the intensity of light incident on the corresponding portion of the sensor 18 has an intermediate level L2 between L1 and L3. The position of the see-through holes 12a-1 and 12b-1 of the lead terminals 12a and 12b thus can be readily detected from the output level of the image sensor 18. The presence of the chip element 13 between the lead terminals 12a and 12b can be readily detected by having reference to the positions of the see-through holes 12a-1 and 12b-1.

If the chip element 13 between the lead terminals 12a and 12b is absent, this can be readily detected since the intensity of incident light between the lead terminals 12a and 12b, i.e., for a corresponding period T1, is L2.

Figure 3:
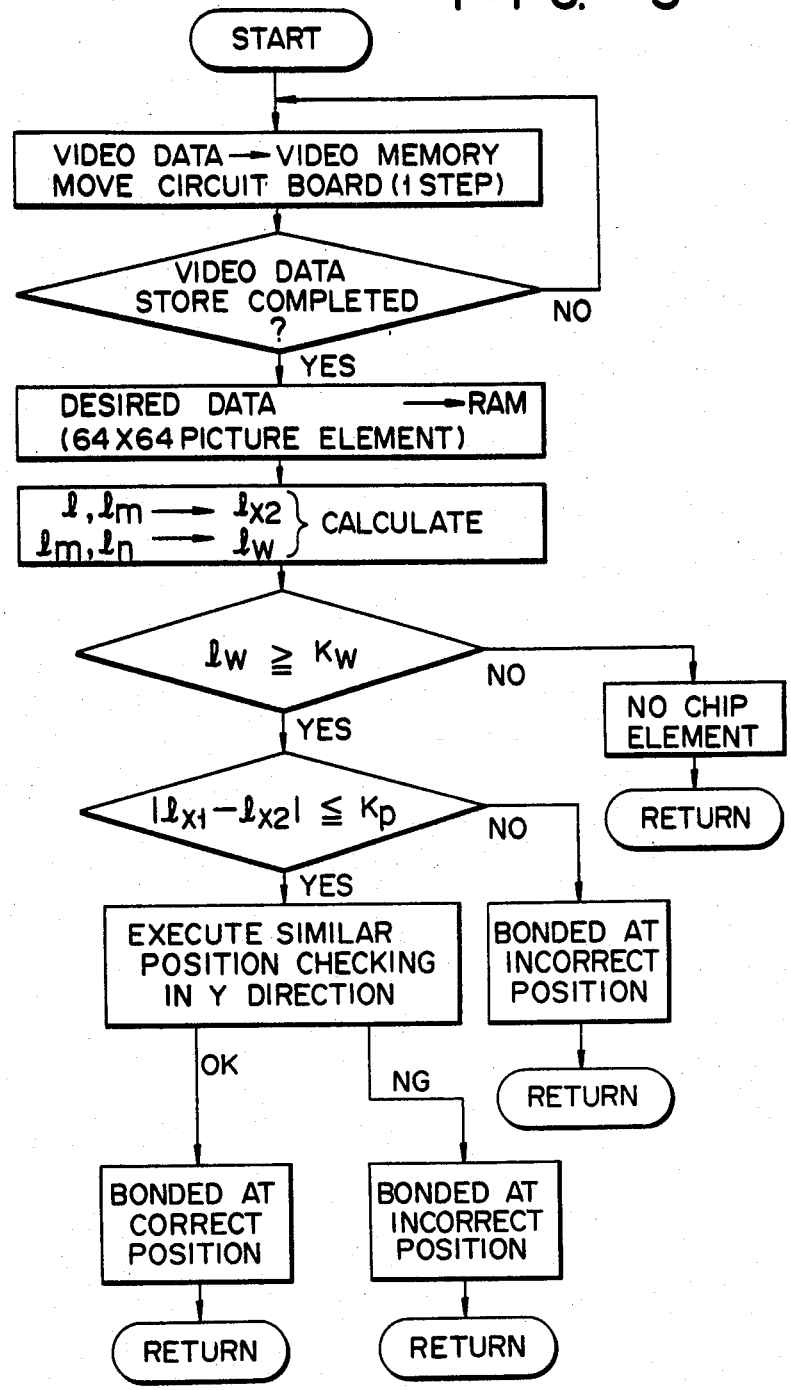
FIG. 3 shows a flow chart showing the operation of the embodiment of FIG. 1.

Examination as to whether the chip element 13 is bonded to the circuit board 11 at a regular position, is effected through a process which will now be described with reference to FIGS. 1, 3 and 4.

When the line scanning of the entire surface of the circuit board 11 by light from the lamp 14 has been completed, the video data of the entire surface of the circuit board 11 that is obtained from the image sensor 18 is stored in the video memory 21. In this state, regular video data of a predetermined image area concerning the lead terminals 12a and 12b of FIG. 1, which is stored in the floppy disk memory 31, is read out by the microprocessor 23. As shown in FIG. 4, the content of this video data has X- and Y-direction dimensions a and b corresponding to 64 scan lines by the image sensor 18. This image area P, with the dimensions of a by b, is very small since the dimensions of the chip element 13 are very small, for instance 3 mm by 1.5 mm. Video data of a detected image area that corresponds to the regular image area P is read out from the video memory 21 and stored in the RAM 29 by the control of the microprocessor 23.

Figure 4:
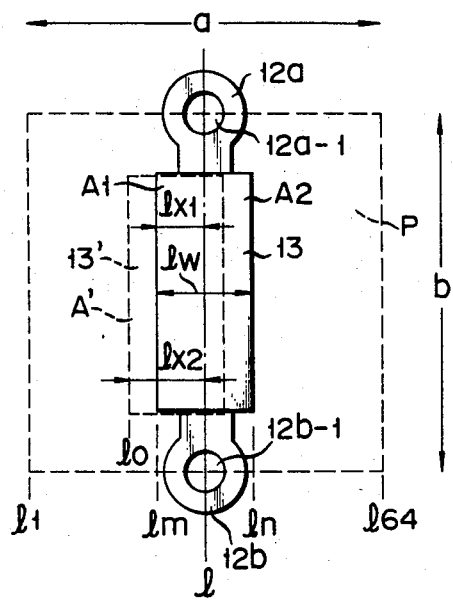
FIG. 4 is a view for explaining the operation of comparing reference pattern data read out from an external memory in FIG. 1 and video data read out from a video memory.

Then the two long sides of detected image area, represented by the video data stored in the RAM 29, are compared with the long sides A1 and A2 of the pattern of the reference video data shown in FIG. 4. If they coincide, it is seen that the chip element 13 is temporarily bonded in the regular position. This can be confirmed using the microprocessor 23 as follows. First, the number of scan lines $l_{x2}$ between the line 1 passing through the center of the see-through holes 12a-1 and 12b-1 in the lead terminals 12a and 12b and the line $l_m$ corresponding to the long side A' of the chip element 13, in the video data stored in the RAM 29, is compared with the number $l_{x1}$ of lines in the reference video data. If the two are equal, the number of lines from the line $l_m$ to the line $l_n$ corresponding to the other long side A2 is compared with the number $l_w$ of lines in the reference video data. If $l_w \geq Kw$ (where Kw is a constant for recognizing the presence or absence of the chip element) is obtained, it is seen that the pattern data of the width $l_w$ is of the chip element 13. If the detected number of lines is considerably smaller than the regular line number, it is seen that the pattern data is not of the chip element 13 but of, for instance, a printed circuit conductor.

If the position of the long side A' of the detected chip element is detected on such a line $l_0$ deviated from the regular line number $l_{x1}$, it is seen that the chip element 13 is temporarily bonded in a position deviated from the regular position by $|l_{x2} - l_{x1}|$. If the deviation $|l_{x1} - l_{x2}|$ is smaller than or equal to a constant Kp, the chip element 13 can be deemed that it is bonded in position in the X-direction.

This position inspection operation in the X-direction is continuously performed by successively incrementing one by one the address designation of the RAM 29. When the position inspection operation in the X-direction is completed, similar position inspection operation may also be performed in Y-direction.

The checking for the positional deviation of the chip elements through comparison of the pattern data of the chip element in the video data stored in the RAM 29 with the pattern data of the chip element in the regular position in the external memory may be done by using various methods as well as the method in the above embodiment.

Figure 5:
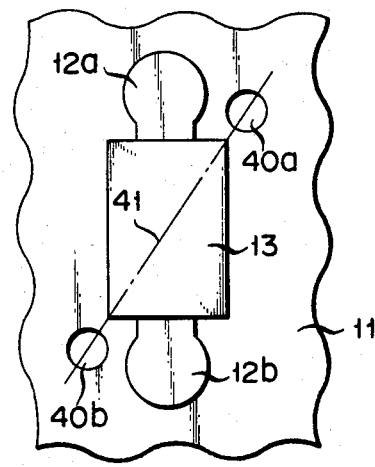
FIG. 5 is a plan view showing part of the circuit board in a different embodiment of the invention.

Further, while in the above embodiment the position of the temporarily bonded chip element 13 is detected by having reference to the see-through holes formed in the lead terminals 12a and 12b and circuit board 11, it is also possible to form see-through holes 40a and 40b as reference holes for detecting the position of the chip element 13 on the circuit board 11 at positions on a diagonal line passing through the chip element 13 independently of the lead terminals 12a and 12b as shown in FIG. 5. Further, it is possible to use blind holes instead of the see-through reference holes. In this case, use is made of the fact that the intensity of incident light from a thin portion of the circuit board 11 is high compared to the rest of the circuit board. Further, it is possible to provide reference marks consisting of a light reflector on the surface of the circuit board 11 facing the image sensor and provide a separate mark illumination light source.

What we claim is:

1. A position examination apparatus for examining the position of miniaturized electronic parts bonded to a transparent circuit board between pairs of lead terminals formed on the surface of the circuit board, the transparent circuit board being formed with a plurality of first see-through holes and the pairs of lead terminals having second see-through holes corresponding to said first see-through holes, comprising:
    means for illuminating said transparent circuit board from one side thereof to provide light passed therethrough, said illuminating means including a light source lamp, a slit plate for converting light from said light source lamp into a narrow beam light and, cylindrical lens for converting the narrow beam light from the slit plate into a parallel beam light;
    means for receiving light from said circuit board which is line-scanned to obtain an image signal representing a line-scanned image of the circuit board;
    an analog-to-digital converter for converting said image signal into digital image data;
    a video memory for storing said digital image data;
    external means for providing reference pattern data of a unit area including said miniaturized electronic part; and
    control means for checking the positional deviation of the miniaturized electronic parts with respect to said first and second see-through holes used as reference marks by reading out digital image data corresponding in position to said reference data from a video memory and comparing the read-out data with said reference pattern data.

2. The position examination apparatus according to claim 1, wherein said circuit board is made of a semitransparent epoxy resin having light illuminated on one surface opposite the other surface on which a miniaturized electronic part is provided.

3. The position examination apparatus according to claim 9, wherein said first and second see-through holes coincide with each other to allow said parallel beam light to pass through the first and second see-through holes.

4. The position examination apparatus according to claim 1, wherein said means for obtaining an image signal includes a linear image sensor for receiving the parallel beam light from said cylindrical lens and having transmitted through said circuit board, and a synchronization signal generating circuit for generating a clock signal for controlling the line scanning operation of said image sensor.

5. The position examination apparatus according to claim 4, wherein said control means includes a microprocessor operating in response to said clock signal and a RAM for storing the digital image data read out from said video memory by said microprocessor.

6. A position examination apparatus for examining the position of a miniaturized electronic part bonded to a transparent circuit board between pairs of lead terminals formed on the surface of the circuit board, the transparent circuit board being formed with a plurality of see-through holes at positions on a diagonal line passing through the miniaturized electronic part independently of the pairs of lead terminals, comprising:
    means for illuminating said transparent circuit board from one side thereof to provide light passed therethrough, said illuminating means including a light source lamp, a slit plate for converting light from said light source lamp into a narrow beam light, and a cylindrical lens for converting the narrow beam light from the slit plate into a parallel beam light;
    means for receiving light from said circuit board which is line-scanned to obtain an image signal representing a line-scanned image of the circuit board;
    an analog-to-digital converter for converting said image signal into digital image data;
    a video memory for storing said digital image data;
    external means for providing reference pattern data of a unit area including said miniaturized electronic part; and
    control means for checking the positional deviation of the miniaturized electronic parts with respect to said see-through holes used as reference marks by reading out digital image data corresponding in position to said reference data from a video memory and comparing the read-out data with said reference pattern data.

7. The position examination apparatus according to claim 6, wherein said circuit board is made of a semitransparent epoxy resin having light illuminated on one surface opposite the other surface on which a miniaturized electronic part is provided.

8. The position examination apparatus according to claim 6, wherein said means for obtaining an image signal includes a linear image sensor for receiving the parallel beam light from said cylindrical lens and having transmitted through said circuit board, and a synchronization signal generating circuit for generating a clock signal for controlling the line scanning operation of said image sensor.

9. The position examination apparatus according to claim 8, wherein said control means includes a microprocessor operating in response to said clock signal and a RAM for storing the digital image data read out from said video memory by said microprocessor.

* * * * *